United States Patent [19]

McKinnie et al.

[11] Patent Number: 4,701,568
[45] Date of Patent: Oct. 20, 1987

[54] PROCESS FOR PREPARING TETRABROMOBISPHENOL-A

[75] Inventors: Bonnie G. McKinnie; Olan W. Mitchell, both of Magnolia Ark.

[73] Assignee: Ethyl Corporation, Richmond, Va.

[21] Appl. No.: 880,598

[22] Filed: Jun. 30, 1986

[51] Int. Cl.⁴ ..................... C07C 39/16; C07C 39/367
[52] U.S. Cl. ..................................... 568/726; 568/779
[58] Field of Search ............................... 568/726, 779

[56] References Cited

U.S. PATENT DOCUMENTS

| | | | |
|---|---|---|---|
| 3,234,289 | 2/1966 | Hennis | 568/726 |
| 3,363,007 | 1/1968 | Majewski et al. | 568/726 |
| 3,546,302 | 12/1970 | Asadorian et al. | 568/779 |
| 3,868,423 | 2/1975 | Montanari et al. | 568/726 |
| 3,929,907 | 12/1975 | Janzon et al. | 568/779 |
| 4,013,728 | 3/1977 | Brackenridge | 568/726 |
| 4,036,894 | 7/1977 | Jenkner | 568/726 |
| 4,451,675 | 5/1984 | Bounds | 568/779 |

*Primary Examiner*—Werren B. Lone
*Attorney, Agent, or Firm*—Donald L. Johnson; John F. Sieberth; W. G. Montgomery

[57]     ABSTRACT

Tetrabromobisphenol-A is made in high purity by contacting a solution of bisphenol-A dissolved in a $C_1$–$C_4$ alkanol with gaseous bromine.

6 Claims, No Drawings

PROCESS FOR PREPARING TETRABROMOBISPHENOL-A

BACKGROUND OF THE INVENTION

Tetrabromobisphenol-A is 4,4'-isopropylidenebis(2,6-dibromophenol). It is a widely used commercial fire retardant. There have been numerous publications on how it can be made. Hennis, U.S. Pat. No. 3,234,289, describes a process in which bisphenol-A (i.e. 4,4'-isopropylidenebisphenol) is placed in a water-alcohol mixture and liquid bromine is added at 22°–28° C. followed by reflux. Majewski et al., U.S. Pat. No. 3,363,007, discloses a process for brominating bisphenol-A in a mixture of water and an alkyl ether of a lower glycol.

Asadorian et al., U.S. Pat. No. 3,546,302, discloses a bromination process conducted in a two-phase solvent having an aqueous phase and an organic phase.

Montanari et al., U.S. Pat. No. 3,868,423, discloses the bromination of isopropylidenebisphenol with liquid bromine and gaseous chlorine in a methanol solvent. Janzon et al., U.S. Pat. No. 3,929,907, discloses the bromination of bisphenols in the presence of aqueous hydrogen peroxide.

Brackenridge, U.S. Pat. No. 4,013,728, teaches a process for brominating bisphenol-A in aqueous acetic acid followed by a heating step. Jenkner, U.S. Pat. No. 4,036,894, discloses bromination of bisphenol-A in acetic acid with recycle of the mother liquor and addition of alkaline or alkaline earth metal acetate.

Production of tetrabromobisphenol-A by dissolving bisphenol-A in methanol and adding liquid bromine is an effective way to make tetrabromobisphenol-A but the product contains various impurities which detract from its commercial value. These impurities include bromophenol, dibromophenol, tribromophenol and hydrolyzable impurities. Thus, a need exists for a process that would lower the amount of these impurities. In pending U.S. application Ser. No. 778,710, filed Sept. 23, 1985, it is reported that the amount of impurities in tetrabromobisphenol-A can be sharply decreased from about 4 weight percent down to about 0.2 weight percent by adding a solution of bromine in methanol to a solution of bisphenol-A dissolved in methanol. This represents a significant advancement in the art. However, there are certain disadvantages inherent in the practice of this process. For example, the bromine-methanol solution cannot be pre-mixed very far in advance of when it is to be reacted with the bisphenol-A since shortly after addition of the liquid bromine to the alcohol, the temperature of the solution rises rapidly to a point which exceeds the boiling point of bromine. At this point, the bromine vaporizes and loss of bromine reactant results. This situation can be ameliorated to a certain degree by cooling the liquid bromine-methanol solution (e.g. under 10° C.) prior to its use or by blending the methanol and bromine in-line just prior to its introduction into the methanol-bisphenol-A solution. However, the former procedure adds an additional step to the process which adds to the cost of producing the tetrabromobisphenol-A product since it requires the use of additional equipment and the latter procedure is not always convenient or available. Accordingly, a welcome contribution to the art would be the provision of a process for making tetrabromobisphenol-A in the same or higher yields and purity as obtained by the aforedescribed liquid bromine in methanol process without the disadvantages of having to use a solution of liquid bromine in methanol as part of the process.

SUMMARY OF THE INVENTION

It has now been discovered that the amount of impurities in tetrabromobisphenol-A can be sharply decreased by using a process in which bisphenol-A is dissolved in a $C_1$ to $C_4$ alkanol and brominated by adding gaseous bromine to the bisphenol-A-alkanol solution. It has been shown that the amount of impurities can be sharply reduced from about 4 weight percent down to as little as 0.1 weight percent.

The amount of alkanol used to disslove the bisphenol-A can vary over a wide range. A useful range is about 2.0–10 parts by weight alkanol per each part bisphenol-A. A more preferred range is about 2.5–4.5 parts by weight alkanol per each part bisphenol-A. Examples of $C_1$ to $C_4$ alkanols include methyl alcohol, ethyl alcohol, n-propyl alcohol, ispropyl alcohol, n-butyl alcohol, isobutyl alcohol, sec-butyl alcohol and t-butyl alcohol. Methanol is a preferred alkanol.

The bromine is introduced into the reaction zone as a vapor, and, if desired, in the presence of an inert carrier gas such as nitrogen or helium to facilitate the addition of the bromine to the reaction mixture. Intimate contact of the halogen molecules with the reaction mixture containing the bisphenol-A reactant dissolved in alkanol can best be obtained by introducing the gas under the surface of the reaction mixture, preferably in an area of high agitation, via a feed pipe or dip tube.

The introduction of the halogen molecules into the reaction mixture is accompanied by the evolution of methyl bromide. It is generally desirable to add the halogen molecules either continuously or in increments so as to obtain a more or less steady rate of evolution of by-product methyl bromide. The methyl bromide vaporizes and can be collected from the off-gas and marketed as a commercial product for its many known uses such as a soil fumigant.

The amount of bromine added to the reaction mixture should be an amount that supplies sufficient bromine to make an acceptable product. The stoichiometric requirement is 4 moles of bromine per mole of bisphenol-A. A useful range in which to operate is about 3.9–4.5 moles of bromine per mole of bisphenol-A and the most preferred range is 4.0–4.1 moles bromine per mole of bisphenol-A.

Bromine may be fed to the reaction mixture at an initial temperature that is ambient or lower although this is not essential. For example, the bromine feed can be started at temperatures from −10° up to about 30° or somewhat higher, e.g. 0°–35° C., if desired. As the feed progresses, the temperature will rise due to the heat of the reaction. Sometime during the feed the temperature will attain reflux conditions and reflux can be continued through the end of the feed of the bromine although reflux is not essential as long as the reaction is continued long enough to substantially complete the bromination. After this, heat can be applied to maintain reflux for a period of time of, for example, about 10 minutes to about 4 hours to assure completion of the reaction.

The reaction is generally carried out under normal pressure. However, it is possible to carry out the process at a slight excess pressure, for example, 2 atmospheres.

Tetrabromobisphenol-A can be recovered from the reaction mixture using conventional methods. For example, the final reaction mixture can be diluted with water and filtered to recover the tetrabromobisphenol-A. The product can then be dried in an oven to remove water, methanol, bromine, HBr and other volatiles.

The following examples serve to illustrate how the process is carried out.

EXAMPLE 1

In a reaction vessel fitted with a condenser, heating mantle, thermometer, stirrer and a dip tube was placed 208 grams of methanol and 54.0 grams bisphenol-A. While stirring, this was heated to reflux and bromine vapor (160 grams) was carried by nitrogen through the dip tube to the reaction mixture containing bisphenol-A over a period of 90 minutes at reflux. Reflux was continued for 10 minutes and then $Na_2SO_3$ was added to destroy the unreacted bromine. A small sample of the product was removed and dissolved in methylene chloride, washed with water and dried over anhydrous sodium sulfate. The methylene chloride was evaporated and N,O-bis(trimethylsilyl) trifluoroacetemide was added to derivitize the product which was then analyzed by gas chromotography.

EXAMPLE 2

In a reaction vessel fitted with a condenser, heating mantle, thermometer, stirrer and a dip tube was placed 170 grams of methanol and 58.1 grams bisphenol-A. While stirring, this was heated to reflux and bromine vapor (159 grams) was carried by nitrogen through the dip tube to the reaction mixture containing bisphenol-A over a period of time of 110 minutes at reflux. Reflux was continued for 10 minutes and then $Na_2SO_3$ was added to destroy the unreacted bromine. A small sample of the product was removed and dissolved in methylene chloride, washed with water and dried over anhydrous sodium sulfate. The methylene chloride was evaporated and N,O-bis(trimethylsilyl) trifluoroacetamide was added to derivitize the product which was then analyzed by gas chromotography.

EXAMPLE 3

In a reaction vessel fitted with a condenser, heating mantle, thermometer, stirrer and dip tube was placed 169 grams of methanol and 58.15 grams bispheol-A. While stirring, this was heated to reflux and bromine vapor (165.3 grams) was carried by nitrogen through the dip tube to the reaction mixture containing bisphenol-A over a period of time of 80 minutes at reflux. Reflux was continued for 15 minutes and then $Na_2SO_3$ was added to destroy the unreacted bromine. A small sample of the product was removed and dissolved in methylene chloride, washed with water and dried over anhydrous sodium sulfate. The methylene chloride was evaporated and N,O-bis(trimethylsilyl) trifluoroacetamide was added to derivitize the product which was then analyzed by gas chromotography.

Analysis of the tetrabromobisphenol-A from Examples 1, 2 and 3 is shown in the following table.

| Compound | Amount (area %) | | |
| --- | --- | --- | --- |
| | Example 1 | Example 2 | Example 3 |
| TBBPA | 99.503 | 97.785 | 98.630 |
| Tribromobisphenol A | 0.337 | 1.921 | 1.114 |
| Dibromobisphenol A | 0.025 | 0.048 | 0.065 |
| Tribromophenol | 0.026 | 0.064 | 0.042 |
| Dibromophenol | 0.053 | 0.079 | 0.085 |
| Bromophenol | trace | trace | trace |
| Others | 0.046 | 0.103 | 0.054 |

The improved process is applicable to the bromination of other bisphenols. These are compounds of the structure

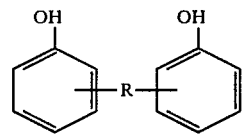

wherein R is a divalent aliphatic hydrocarbon group of 1-4 carbon atoms or a direct bond between the two benzene rings. Representative examples are 4,4'-methylenebisphenol, 2,2'-methylenebisphenol, 2,4'-methylenebisphenol, 4,4'-ethylidenebisphenol, 2,2'-ethylidenebisphenol, 2,4'-ethylidenebisphenol, 2,2'-isopropylidenebisphenol, 2,4'-isopropylidenebisphenol, 4,4'-butylidenebisphenol, 2,2'-butylidenebisphenol, 4,4'-biphenol, 2,2'-biphenol, 2,4'-biphenol, and the like. These bisphenols can be substituted for the bisphenol-A, i.e. 4,4'-isopropylidenebisphenol, used in the foregoing description and examples of the present invention. All the products can be used as fire retardants in a broad range of organic materials normally susceptible to combustion in the presence of air and ignition source.

We claim:

1. A process for brominating bisphenol-A to make mainly tetrabromobisphenol-A while minimizing the formation of by-products, said process comprising:
   (a) dissolving bisphenol-A in a $C_1$-$C_4$ alkanol in a weight ratio of about 2.0-10 parts alkanol per each part bisphenol-A,
   (b) contacting the bisphenol-A solution with gaseous bromine with stirring at a reaction temperature initially of up to about 35° C. and finally at reflux, and
   (c) recovering tetrabromobisphenol-A.

2. The process of claim 1 wherein said bromine is added at a reaction temperature initially at about −10° C. to 35° C. and finally at reflux.

3. The process of claim 1 wherein said alkanol:bisphenol-A weight ratio is about 2.5-4.5.

4. The process of claim 3 wherein said alkanol is methanol.

5. The process of claim 4 wherein said bromine is added in an amount to provide about 4 moles of bromine per mole of bisphenol-A.

6. A process for brominating a bisphenol to make mainly tetrabromobisphenol while minimizing formation of by-products, said process comprising:
   (a) dissolving said bisphenol in a $C_1$-$C_4$ alkanol in a weight ratio of about 2.0-10 parts alkanol per each part bisphenol,
   (b) contacting the bisphenol solution with gaseous bromine with stirring at a reaction temperature initially of up to about 35° C. and finally at reflux, and
   (c) recovering tetrabromobisphenol.

* * * * *